United States Patent
Chao et al.

(10) Patent No.: US 7,399,119 B2
(45) Date of Patent: Jul. 15, 2008

(54) METHOD AND SYSTEM FOR MEASURING AN ALIGNMENT OF A DETECTOR

(75) Inventors: Edward Henry Chao, Oconomowoc, WI (US); Thomas Louis Toth, Brookfield, WI (US); Tanvi Kachhy, Milwaukee, WI (US); Bruce Matthew Dunham, Mequon, WI (US); Abdelaziz Ikhlef, Waukesha, WI (US)

(73) Assignee: General Electric Company, Schenectady, NY (US)

( * ) Notice: Subject to any disclaimer, the term of this patent is extended or adjusted under 35 U.S.C. 154(b) by 431 days.

(21) Appl. No.: 11/230,001

(22) Filed: Sep. 19, 2005

(65) Prior Publication Data

US 2007/0081148 A1    Apr. 12, 2007

(51) Int. Cl.
*A61B 6/08* (2006.01)
*G21K 1/02* (2006.01)
*G21K 1/12* (2006.01)

(52) U.S. Cl. .......................... 378/205; 378/147; 378/19; 378/901

(58) Field of Classification Search .................. 378/4, 378/20, 147–153, 205, 207, 901, 19, 98.8, 378/145
See application file for complete search history.

(56) References Cited

U.S. PATENT DOCUMENTS

| | | | |
|---|---|---|---|
| 4,809,314 A | 2/1989 | Steele et al. | |
| 5,469,429 A | 11/1995 | Yamazaki et al. | |
| 6,056,437 A | 5/2000 | Toth | |
| 6,322,249 B1 | 11/2001 | Wofford et al. | |
| 6,411,677 B1 | 6/2002 | Toth et al. | |
| 7,257,187 B2 * | 8/2007 | Chao et al. ..................... | 378/19 |
| 2002/0015474 A1 * | 2/2002 | Tybinkowski et al. ....... | 378/153 |
| 2002/0146093 A1 * | 10/2002 | Williams ..................... | 378/205 |
| 2004/0213380 A1 * | 10/2004 | Shaw et al. .................. | 378/145 |
| 2007/0041508 A1 * | 2/2007 | Tubbs ......................... | 378/207 |

* cited by examiner

*Primary Examiner*—Irakli Kiknadze
(74) *Attorney, Agent, or Firm*—Armstrong Teasdale LLP

(57) ABSTRACT

A method for measuring an alignment of a detector is described. The method includes determining, by a processor, the alignment of the detector with respect to a collimated radiation beam. The determination of the alignment is based on a plurality of signals from a first cell of the detector and a second cell of the detector, and is independent of a shape of the collimated radiation beam.

20 Claims, 10 Drawing Sheets

METHOD AND SYSTEM FOR MEASURING AN ALIGNMENT OF A DETECTOR

BACKGROUND OF THE INVENTION

This invention relates generally to a medical imaging system, and more particularly, to a method and system for measuring an alignment of a detector of a medical imaging system.

A medical imaging system generally includes an illuminating source, a beam collimator and a detector. The detector detects a beam coming from illuminating source through the beam collimator. In case the detector is not aligned with the beam, the medical imaging system produces images of degraded quality and may also lead to extra dosage of radiations to a patient. The detector, therefore, is to be aligned with the illuminating beam.

Present techniques provide alignment of the detector as a single unit. However, it is difficult for the present techniques to align field replaceable modules of the detector. Additionally, the present techniques rely on experimentally determined scale factors which are time-consuming and computationally expensive to obtain. Adjustment of the present techniques for more sensitive measurements generally includes using new scaling factors and hence results in additional effort and time.

BRIEF DESCRIPTION OF THE INVENTION

In an exemplary embodiment of the invention, a method for measuring an alignment of a detector is described. The method includes determining, by a processor, the alignment of the detector with respect to a collimated radiation beam. The determination of the alignment is based on a plurality of signals from a first cell of the detector and a second cell of the detector, and is independent of a shape of the collimated radiation beam.

In another exemplary embodiment of the invention, a system for measuring an alignment of a detector is described. The system includes a processor configured to determine the alignment of the detector with respect to a collimated radiation beam based on a plurality of signals from a first cell of the detector and a second cell of the detector. The processor is configured to determine the alignment independent of a shape of the collimated radiation beam.

DETAILED DESCRIPTION OF THE INVENTION

Various embodiments of the invention provide a method and a system for measuring an alignment of a detector. In various embodiments of the invention, the detector may be a part of an x-ray imaging system, for example, a Computed Tomography (CT) imaging system. The method is performed by determining by a processor the alignment of the detector based on electrical signals from cells of the detector.

Figure 1:
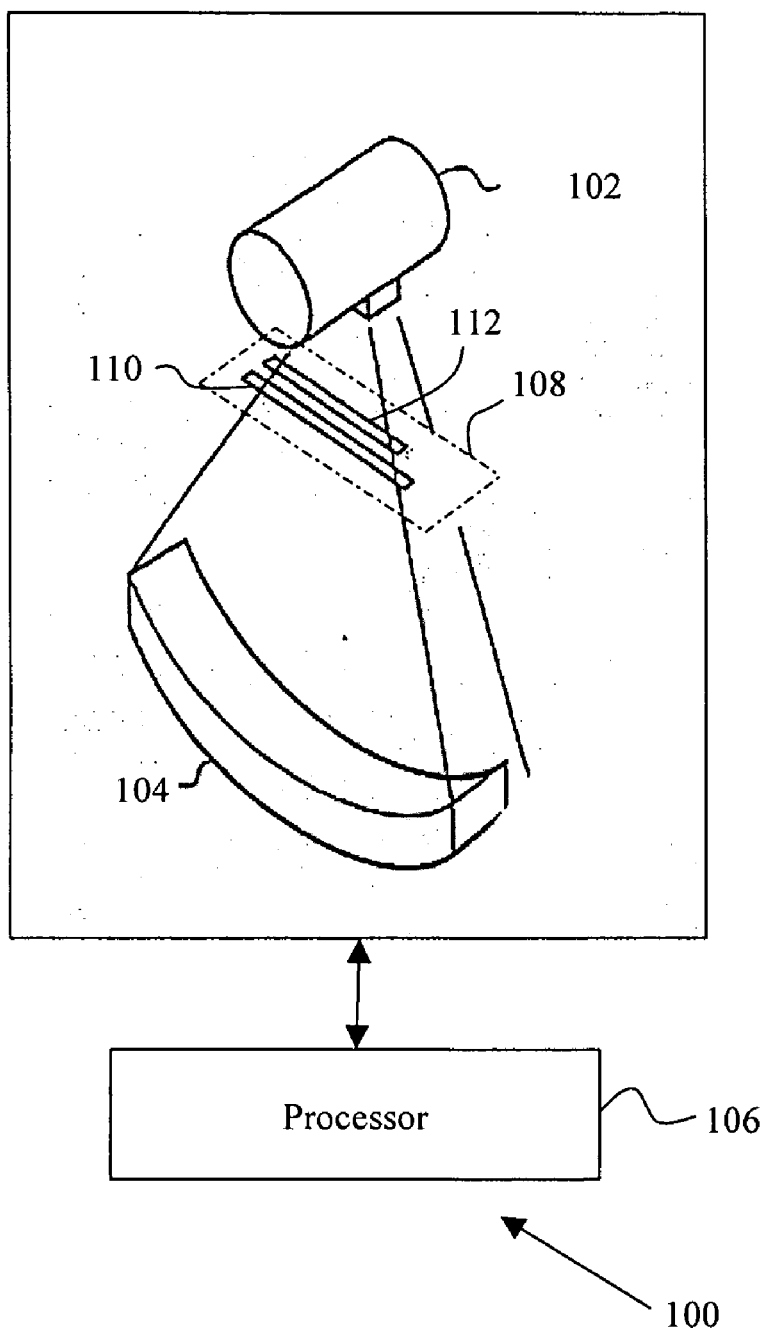
FIG. 1 is a block diagram of an x-ray imaging system for measuring an alignment of a detector, in accordance with an embodiment of the invention.

FIG. 1 is a block diagram of an x-ray imaging system 100 for measuring an alignment of a detector, in accordance with an embodiment of the invention. X-ray imaging system 100 includes an x-ray source 102, a detector 104 and a processor 106. In an embodiment of the invention, x-ray imaging system 100 further includes a collimator 108 having movable cams 110 and 112. X-ray source 102 produces x-ray beams and projects them towards detector 104. Collimator 108 collimates these x-ray beams and movable cams 110 and 112 of collimator 108 sweep the collimated x-ray beam (also referred to as collimated radiation beam) over detector 104. Detector 104 generates the electrical signals corresponding to the flux of the collimated x-ray beam impinging on a surface of detector 104. The electrical signals generated by detector 104 are received by processor 106. Processor 106 then measures the alignment of the detector based on the electrical signals generated by detector 104.

Detector 104 includes a plurality of rows and columns and hence forms a matrix. Each element of the matrix of detector 104 is a detector cell. Each detector cell of detector 104 is configured to generate an electrical signal when a flux of the collimated x-ray beam impinges a surface of the detector cell.

Processor 106 may be a computer, a microcontroller, a microcomputer, a programmable logic controller, an application specific integrated circuit, or any other programmable circuit.

In an embodiment of the invention, movable cams 110 and 112 of collimator 108 may be tapered. Further, each movable cam 110 and 112 can be independently positioned to alter a position and width of x-ray beams relative to detector 104. Each cam 110 and 112 is positioned by a plurality of motors (not shown). A first one of the motors is coupled via a belt to cam 110 and a second one of the motors is coupled via another belt to cam 112.

Figure 2:
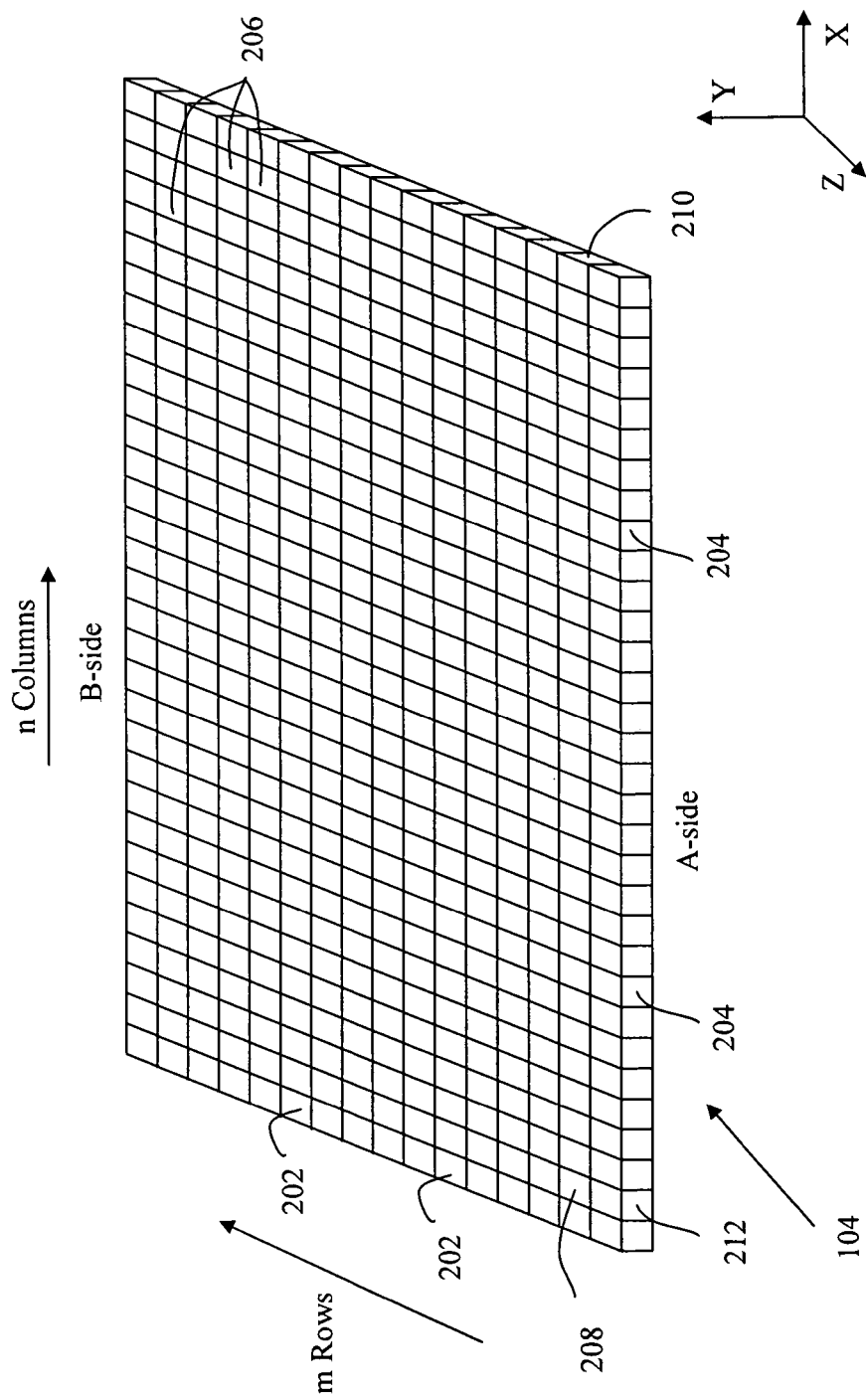
FIG. 2 is an exemplary detector which may be positioned with the x-ray imaging system of FIG. 1.

FIG. 2 is an isometric view of detector 104 when detector 104 is confined to a single plane. Detector 104 includes a plurality of rows 202 and plurality of columns 204 and hence forms a matrix of detector cells 206. A detector cell 208, as shown in FIG. 2, lies on a second row 210 and a second column 212 of detector 104. In an embodiment of the invention, detector 104 includes m rows 202 and n columns 204 of detector cells 206 such that detector 104 has a matrix of m×n detector cells 206. In an exemplary embodiment, m=16 and n=32 such that detector 104 includes 512 detector cells 206. Although detector 104 is illustrated as including sixteen rows 202 (m=16) and thirty-two columns 204 (n=32) of detector cells 206, detector 104 may include any quantity greater than or equal to two rows 202 and any quantity of columns 204. In an embodiment of the invention, detector 104 may also include a plurality of detector modules, where each detector module includes a subset of columns 204. For example, a detector with 16 rows and 32 columns may include two detector modules, each detector module having 16 rows and 16 columns.

Figure 3:
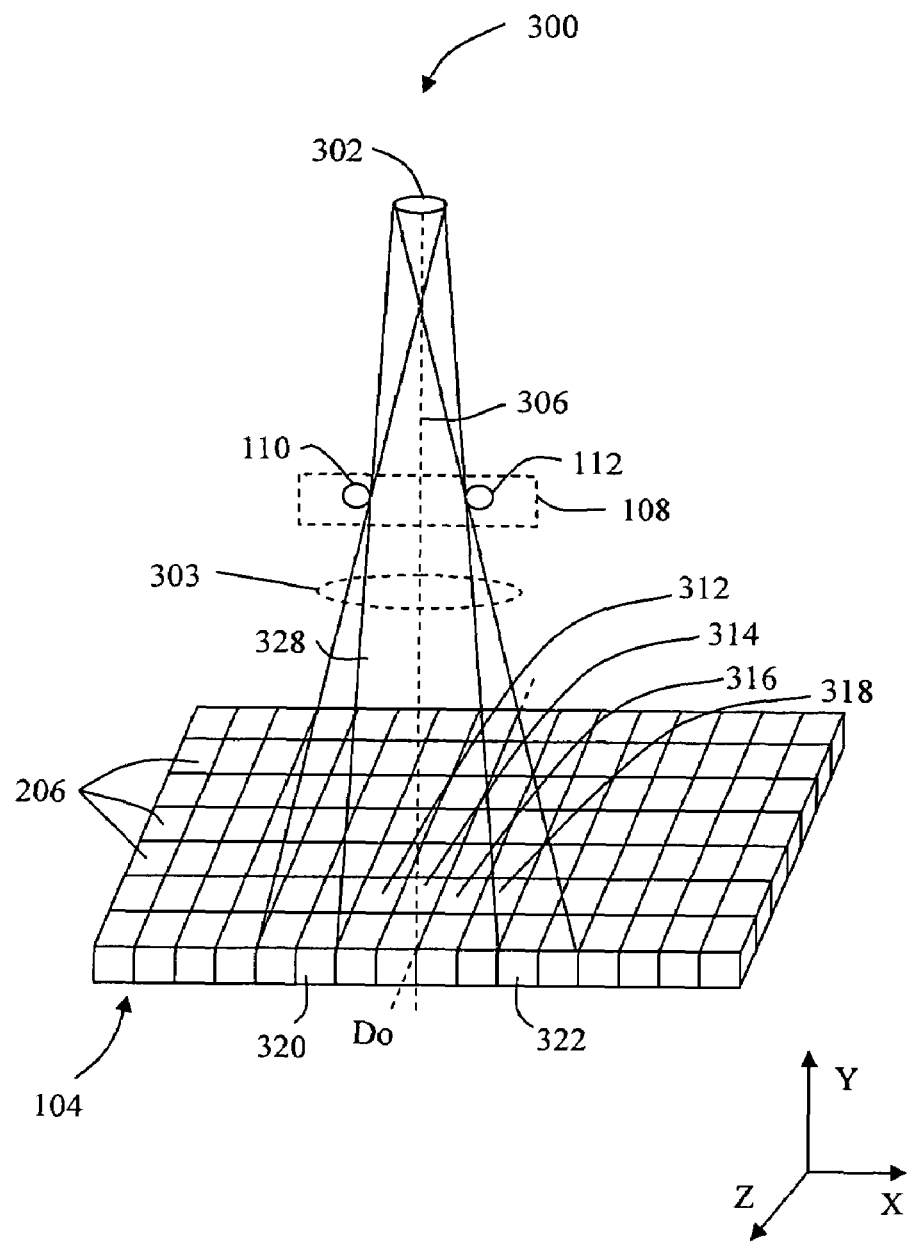
FIG. 3 is a schematic view of a portion of the x-ray imaging system, in accordance with an embodiment of the invention.

FIG. 3 is a schematic view of a portion of the x-ray imaging system 100, in accordance with an embodiment of the invention. X-ray source 102 (FIG. 1) is located at a focal spot 302. X-ray imaging system 100 further includes detector 104, a plurality of detector cell rows 312, 314, 316, 318, 320, and 322, and collimator 108 having movable cams 110 and 112.

X-rays emanate from focal spot 302 of x-ray source 102 (shown in FIG. 1). The x-rays are collimated by collimator 108 to generate a collimated x-ray beam 303 having edges defined by a penumbra of the collimated x-ray beam 303. In the penumbra, flux of the collimated x-ray beam 303 reduces gradually to zero. Collimated x-ray beam 303 is projected toward detector 104. A portion of collimated x-ray beam 303 forms the penumbra on detector cell rows 320 and 322. Also, a portion of collimated x-ray beam 303 forms an umbra on detector cell rows 312, 314, 316, and 318. In the umbra of collimated x-ray beam 303, the flux of the collimated x-ray beam 303 is a constant. A fan beam plane 328 contains a centerline of focal spot 302 and a centerline 306 of collimated x-ray beam 303 that connects the center of focal spot 302 with the center between the collimator cams 110 and 112. Various embodiments of the invention provide methods for alignment of fan beam plane 328 with a centerline $D_0$ of detector 104. Each detector cell 206 of detector 104 has a gain value and the gain value affects an electrical signal generated by detector cell 206. Each detector cell 206 may have a different gain value than at least one another detector cell 206. When a first detector cell 206 has a different first gain value than a second gain value of at least a second detector cell 206, the gain values of the first and second detector cells 206 are accounted for by dividing the electrical signal from the first detector cell 206 by the first gain value and by dividing the electrical signal from the second detector cell 206 by the second gain value. In an alternative embodiment, each detector cell 206 has the same gain value as any other detector cell 206.

The flux of the collimated x-ray beam 303 impinging on the detector cells 206 depends on whether detector cell 206 is under the penumbra or the umbra. The flux of the collimated x-ray beam 303 impinging on the detector cells 206 changes when movable cams 110 and 112 are moved or swept over detector cells 206.

In an embodiment of the invention, as movable cams 110 and 112 of collimator 108 come close to each other, detector cells 206 located along detector cell rows 312 and 318, originally under the umbra, gradually shift under the penumbra. Hence, the flux of collimated x-ray beam 303 impinging the surface of detector cells 206 located along detector cell rows 312 and 318 decreases, causing the signals generated by the detector cells to decrease gradually.

Figure 4:
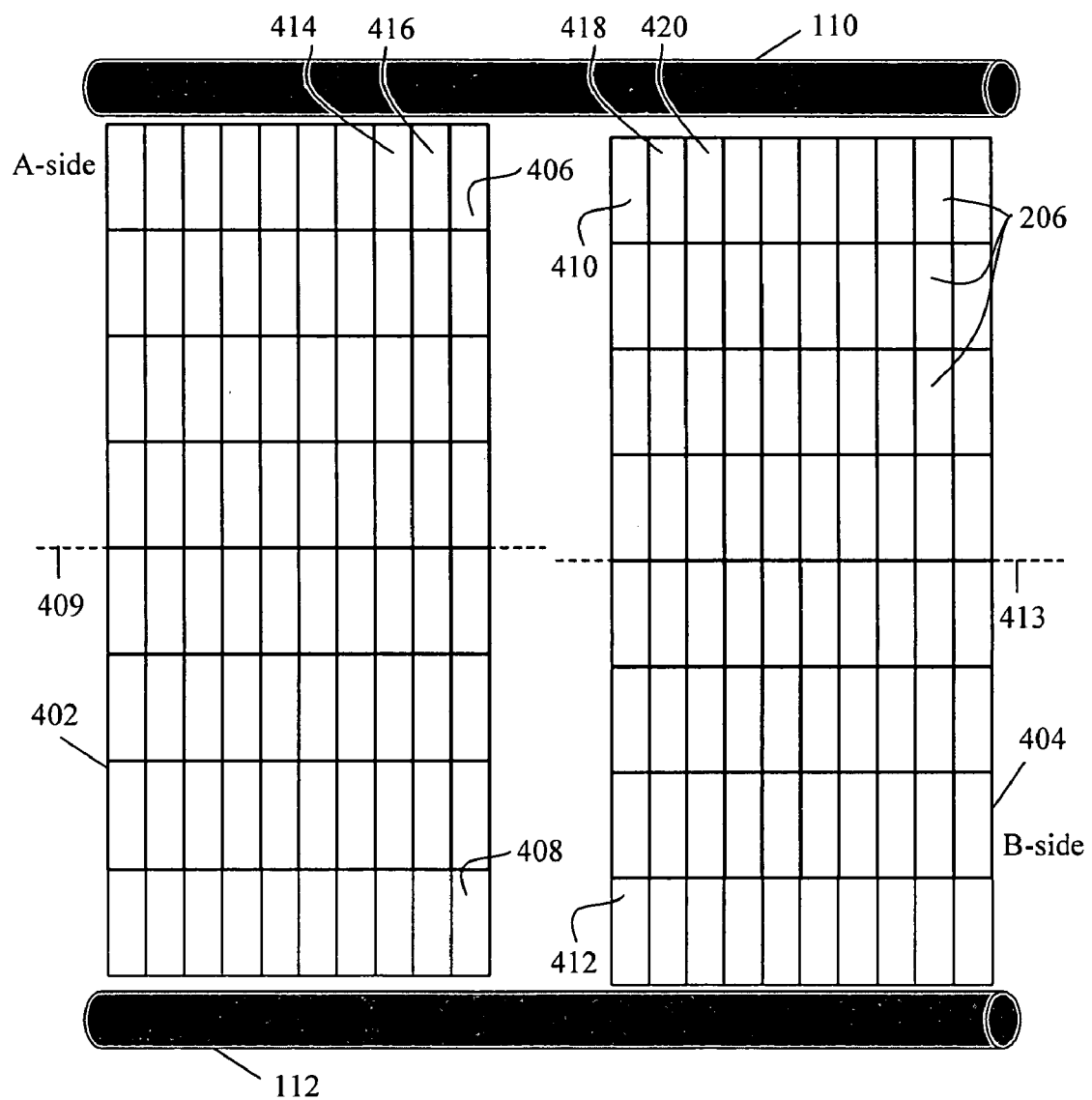
FIG. 4 is a diagram illustrating a detector with two detector modules, in accordance with an embodiment of the invention.

FIG. 4 is a diagram illustrating detector 104 with two detector modules, in accordance with an embodiment of the invention. Detector 104 includes a first detector module 402 and a second detector module 404. Both detector modules 402 and 404 have a plurality of rows and columns forming a matrix of detector cells 206.

In an embodiment of the invention, a first detector cell 406 is located at a top detector row, on A-side, of first detector module 402 and second detector cell 408 is located at a bottom detector row, on B-side of first detector module 402. First detector cell 406 and second detector cell 408 are on the same column of first detector module 402 and equal and oppositely located from a center-line 409 of first detector module 402. Also, a third detector cell 410 is located at a top detector row, on A-side, of second detector module 404 and fourth detector cell 412 is located at a bottom detector row, on B-side of second detector module 404. Third detector cell 410 and fourth detector cell 412 are on the same column of second detector module 404 and equal and oppositely located from a center-line 413 of second detector module 404. Further, first detector module 402 includes detector cell 414 and 416. Detector cells 414 and 416 are located at a top detector row, on A-side, of first detector module 402. Similarly, second detector module 404 includes detector cells 418 and 420. Detector cells 418 and 420 are located at a top detector row, on A-side, of second detector module 404.

First detector cell 406 generates a first signal, corresponding to a position of movable cam 110, when the collimated x-ray beam 303 impinges a surface of first detector cell 406. Similarly, third detector cell 410 generates a third signal corresponding to a position of movable cam 110, when the collimated x-ray beam 303 impinges a surface of third detector cell 410. An amplitude or intensity of the first signal generated by first detector cell 406 and the third signal generated by third detector cell 410 decreases when movable cams 110 and 112 sweep over the first and third detector cells 406 and 410. Hence, a first signal curve for first detector cell 406 and a third signal curve for third detector cell 410, including signals generated at different positions of movable cam 110 are obtained. Similarly, a second signal curve for second detector cell 408 and a fourth signal curve for fourth detector cell 412 are obtained when movable cam 112 sweeps over the second detector cell 408 and fourth detector cell 412.

Figure 5:
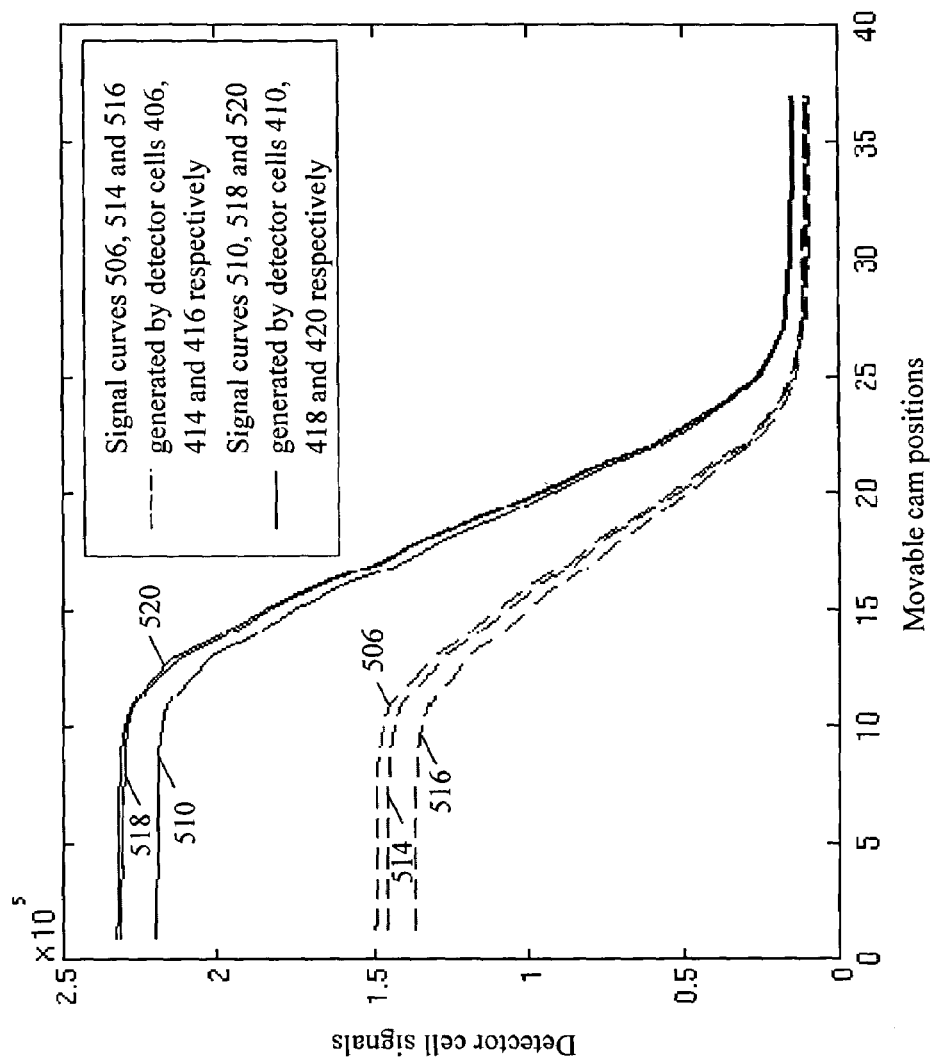
FIG. 5 is a graph illustrating signal curves generated by detector cells of the detector of FIG. 4.

FIG. 5 is a graph illustrating the signal curves 506, 514, 516, 510, 518, and 520 generated by six detector cells 406, 414, 416, 410, 418, and 420 of detector 104. Detector cells 406, 414 and 416 are located adjacent to each other on the top detector row, on A-side, of first detector module 402. Also, detector cells 410, 418 and 420 are located on the top detector row, on A-side, of second detector module 404. Signal curves 506, 514, 516, 510, 518, and 520 generated by the detector cells 406, 414, 416, 410, 418, and 420 are plotted against the different positions of movable cam 110. In an embodiment of the invention, the movable cams 110 and 112 are swept toward centerline $D_0$ of detector 104 in successively discrete positions with each position spanning 50 microns from a preceding position. In an alternative embodiment, the movable cams 110 and 112 are swept toward centerline $D_0$ detector 104 in successively continuous positions with each position progressing towards detector 104. Amplitudes of signals generated by detector cells 406, 414, 416, 410, 418 and 420, start decreasing as movable cam 110 sweeps over them. Further, for first detector module 402, the signal curves 506, 514, and 516 generated from signals produced by one of the detector cells 406, 414 and 416 are different because any one of the detector cells 406, 414, and 416 has a different gain value than gain values of the remaining of the detector cells 406, 414, and 416. Similarly, for second detector module 404, the signal curves 510, 518, and 520 generated from signals produced by one of the detector cells 410, 418 and 420 are different because any one of the detector cells 406, 414, and 416 has a different gain value than gain values of the remaining of the detector cells 410, 418, and 420. In an embodiment of the invention, processor 106 normalizes signal curves generated by a plurality of detector cells within a detector module by dividing a value of a signal generated by one the detector cells by a maximum value of a signal generated by one of the detector cells. Normalization is performed on a signal curve, generated by a detector cell, to make the signal curve independent of varying gain values of a plurality of detector cells.

Figure 6:
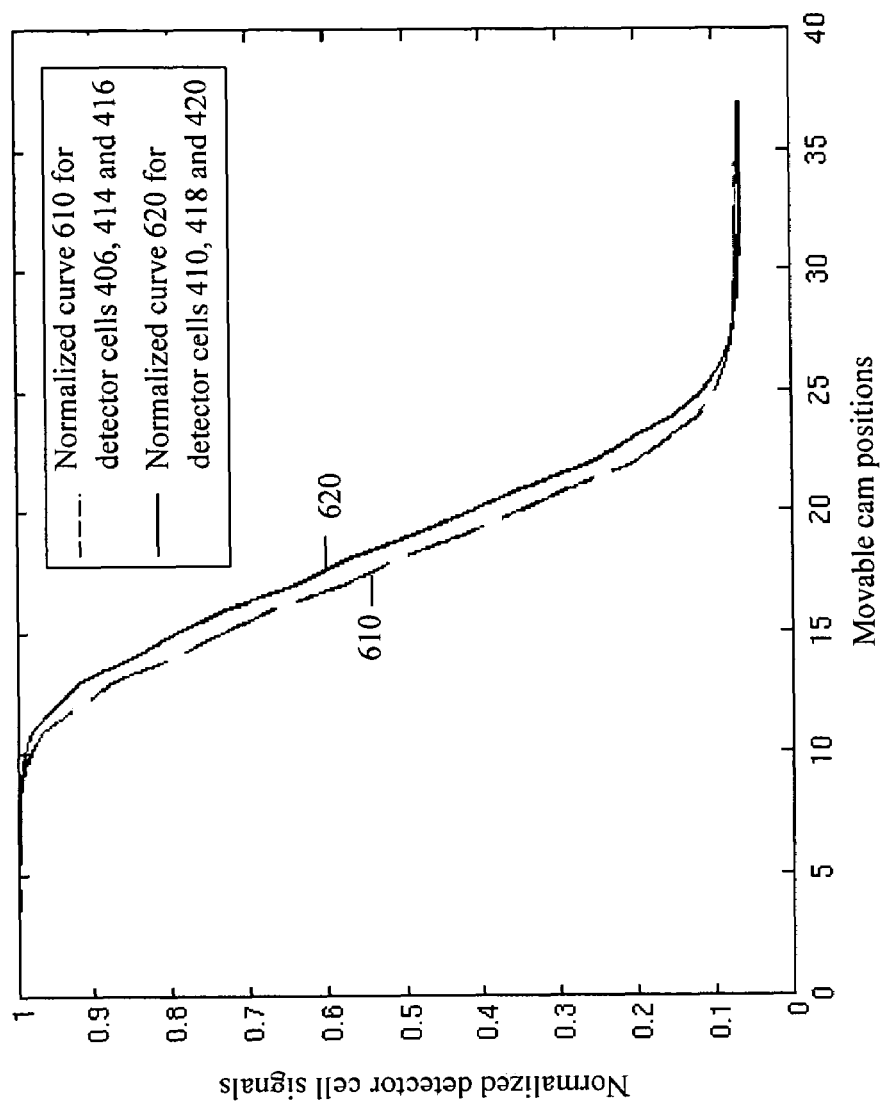
FIG. 6 is a graph showing normalized signal curves generated by normalizing the signal curves of FIG. 5.

FIG. 6 is a graph 600 showing a plurality of normalized signal curves 610 and 620. A Y-axis of the graph 600 shows the normalized detector cell signal values. An X-axis of the graph 600 shows a number of different positions of movable cam 110. Normalized values of signals generated from signals provided by detector cells 406, 414 and 416 overlap each other to generate signal curve 610. Similarly, normalized values of signal curves 510, 518, and 520 generated from signals provided by detector cells 410, 418 and 420 overlap each other to generate signal curve 620. There is a difference in the signals generated by detector cells 406, 414 and 416 of first detector module 402 and detector cells 410, 418 and 420 of second detector module 404, as first detector module 402 and second detector module 404 are not aligned with each other. For example, first detector module 402 is closer to movable cam 110 as compared to second detector module 404.

In various embodiments of the invention, processor 106 measures alignment of first detector module 402 and second detector module 404 by determining a difference between a position of movable cam 110 at which the normalized signal curve 610 has a signal amplitude or intensity input via an input device (not shown), such as a keyboard or a mouse, into processor 106 and a position of movable cam 110 at which the normalized signal curve 620 has the same signal intensity. In an embodiment of the invention, positions of movable cam 110 are measured at 0.5 level of maximum signal intensities generated from signals received from detector cells 406, 414, and 416, and of maximum signal intensities from signals received from detector cells 410, 418, and 420. Processor 106 calculates a difference in the positions of movable cam 110 at which the normalized signal curve 610 and the normalized signal curve 620 have the same signal intensity, such as 0.5, to provided a direct distance measurement of misalignment between first detector module 402 and second detector module 404.

In yet another embodiment of the invention, a position, x1, of movable cam 110, which sweeps first detector cell 406 and a position, x2, of movable cam 112, which sweeps second detector cell 408, at a pre-specified signal intensity, is determined by processor 106. In an alternative embodiment, the position x1 of movable cam 110 is determined when cam 110 sweeps a detector cell of first detector module 402 that is oppositely located on the other side of center-line 409 from second detector cell 408 but not at the same distance from center-line 409 as that of second detector cell 408. In another alternative embodiment, the position x2 of movable cam 112 is determined when cam 112 sweeps a detector cell of first detector module 402 that is oppositely located on the other side of center-line 409 from first detector cell 406 but not at the same distance from center-line 409 as that of first detector cell 406. A pre-specified signal intensity is input via an input device (not shown), such as a keyboard or a mouse, into processor 106. Positions x1 and x2 are positions from center-line 306 of collimated x-ray beam 303. Both x1 and x2 are positive values as measured from centerline 306 of collimated x-ray beam 303. First detector module 402 is determined to be aligned with collimated x-ray beam 303 if value of equation (1) is zero:

$$(x1-x2)/2 \quad (1)$$

Otherwise, if the value of equation (1) is not zero, equation (1) gives a distance measurement of the misalignment of center-line 409 of first detector module 402 with the centerline 306 of the collimated x-ray beam 303. In one embodiment, equation (1) applies to detector cells 406 and 408, which are located at equal and opposite distances from the centerline $D_0$ of the detector 104. However, in an alternative embodiment, equation (1) is modified to apply to detector cells which are a known, but unequal, distance from the centerline $D_0$ of detector 104. Additionally, the value of equation (1) is independent of a shape of collimated radiation beam 303. Indeed, in various embodiments of this invention, the shape of the collimated radiation beam 303 is continually changed as the collimator cams 110 and 112 are moved. For example, the value of equation (1) does not need to be recalculated when the shape of collimated x-ray beam 303 changes from encompassing 4 rows of detector cells of first detector module 402 to 2 rows of first detector module 402. As another example, the value of equation (1) stays the same before and after changing the shape of collimated x-ray beam from encompassing 2 rows of detector cells of first detector module 402 to 4 rows of first detector module 402. Shape of collimated x-ray beam 303 is not a factor in determining the value of equation (1).

In still another embodiment of the invention, positions of movable cams 110 and 112, at a pre-specified signal intensity, on normalized curves generated for a plurality of detector cells, which are located on first detector module 402 and second detector module 404, are used to determined the alignment of detector 104 with respect to the collimated x-ray beam 303.

Figure 7:
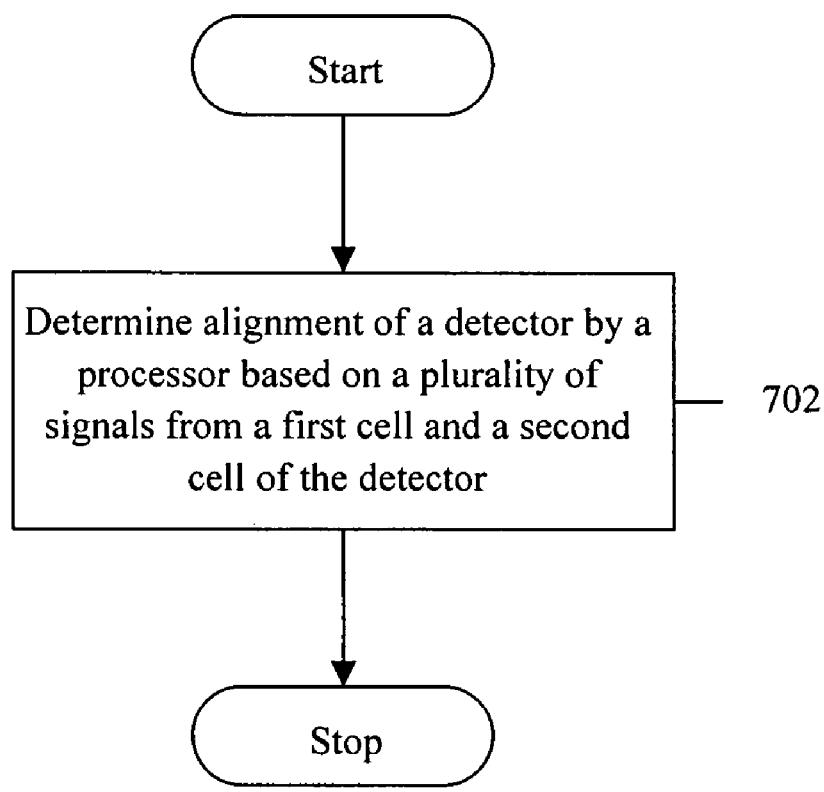
FIG. 7 is a flowchart of a method for measuring an alignment of a detector, in accordance with an embodiment of the invention.

FIG. 7 is a flowchart of a method for measuring the alignment of detector 104, in accordance with an embodiment of the invention. At 702, processor 106 determines alignment of detector 104 based on a plurality of signals from a first and a second detector cell of a detector module of detector 104. A first detector cell and a second detector cell, located along a same column, are at an equal and opposite distance from a center-line of a detector module of detector 104. For example, 406 and 408 may be the first and the second detector cells respectively.

Figure 8:
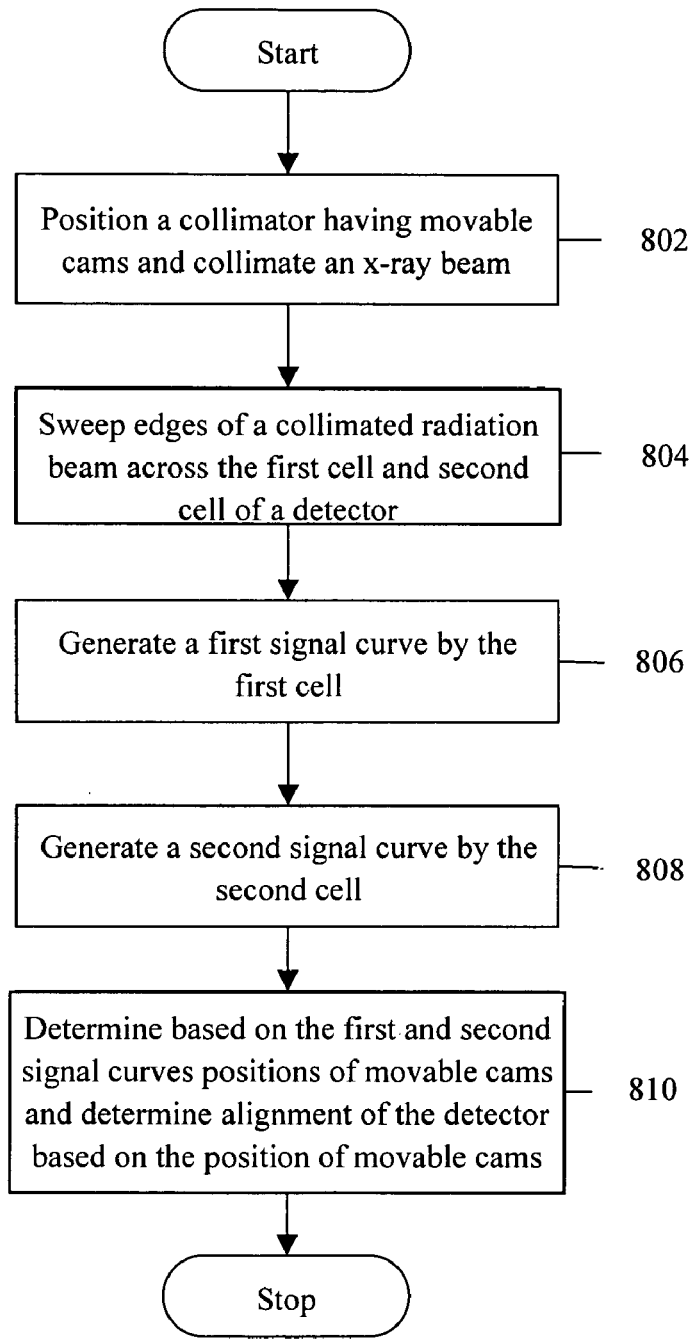
FIG. 8 is a flowchart of a method for measuring an alignment of a detector, in accordance with another embodiment of the invention.

FIG. 8 is a flowchart of a method for measuring the alignment of a detector, in accordance with an embodiment of the invention. At 802, collimator 108 having movable cams 110 and 112 is positioned over detector 104. Movable cams 110 and 112 are initially placed so that detector cells 206 are under the umbra. Collimator 108 also collimates x-ray beams 303. At 804, movable cams 110 and 112 sweep the edges of collimated x-ray beam 303 over first detector cell 406 and second detector cell 408. In an alternative embodiment, cams 110 and 112 are initially placed at a position to shield detector cells 406 and 408 from collimated x-ray beam 303, and cams 110 and 112 are sweeped away from center-lines 409 and 413 so that detector cells 406 and 408 pass through the penumbra to perform methods for measuring the alignment of a detector. In yet another alternative embodiment, cam 110 is initially placed at a first position to shield detector cell 406 from collimated x-ray beam 303, cam 112 is initially placed at a second position so that detector cell 408 lies within the umbra, and cams 110 and 112 are sweeped to place cam 110 at a third position within the umbra, to place cam 112 at a fourth position shielding detector cell 408 from collimated x-ray beam 303, and to apply the methods for measuring the alignment of a detector.

At 806, first detector cell 406 generates a first signal curve. The first signal curve contains values of signals generated by first detector cell 406 as edges of collimated x-ray beam 303 are swept by movable cam 110 over first detector cell 406. At 808, second detector cell 408 generates a second signal curve. The second signal curve contains values of signals generated by second detector cell 408 as edges of collimated x-ray beam 303 are swept by movable cam 112 over second detector cell 408. At 810, processor 106 determines an alignment of first detector module 402 of detector 104 based on positions of movable cams 110 and 112 at which the first and second signal curves measure the same pre-specified signal intensity. A difference between a position of movable cam 110, corresponding to the pre-specified signal intensity on the first signal curve, and the position of movable cam 112, corresponding to the pre-specified signal intensity on the second signal curve, gives a direct distance measurement of alignment of first detector module 402 of detector 104 with respect to the centerline 306 of collimated x-ray beam 303. Similarly, alignment of second detector module 404 with respect to the centerline 306 of collimated x-ray beam 303 is also determined. It is noted that 802 and 804 are performed by the motors under control of processor 106 and 810 is performed by processor 106.

In various embodiments of the invention, direct distance measurement of misalignment at the movable cams level is converted to a distance measurement at the detector level. The direct distance measurement, obtained by calculating a difference, signed average or any other mathematical function, is multiplied by a scaling factor to obtain the measure of alignment at the detector level. The scaling factor may be, for example, but is not limited to, a ratio of the distance between focal spot 302 and collimator 108 and the distance between collimator 108 and detector 104.

Figure 9:
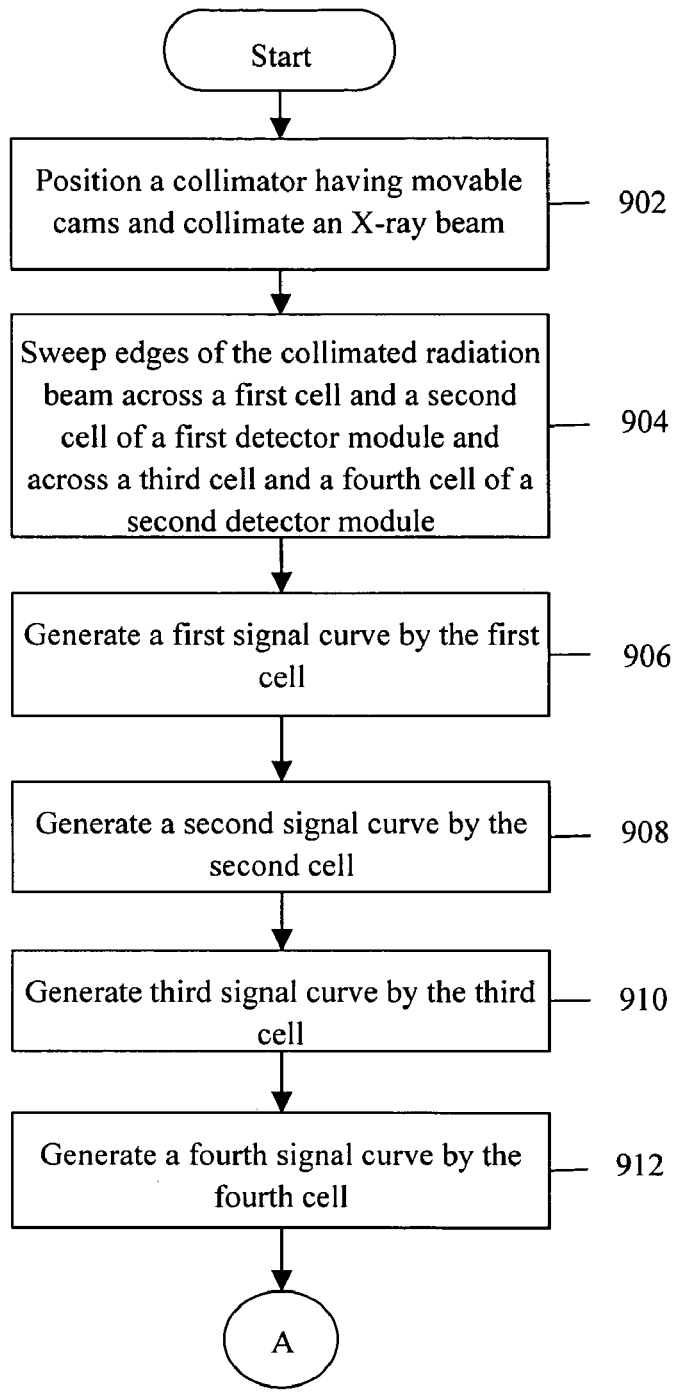
FIG. 9 illustrates a flowchart of a method for measuring an alignment of a detector, in accordance with yet another embodiment of the invention.
Figure 10:
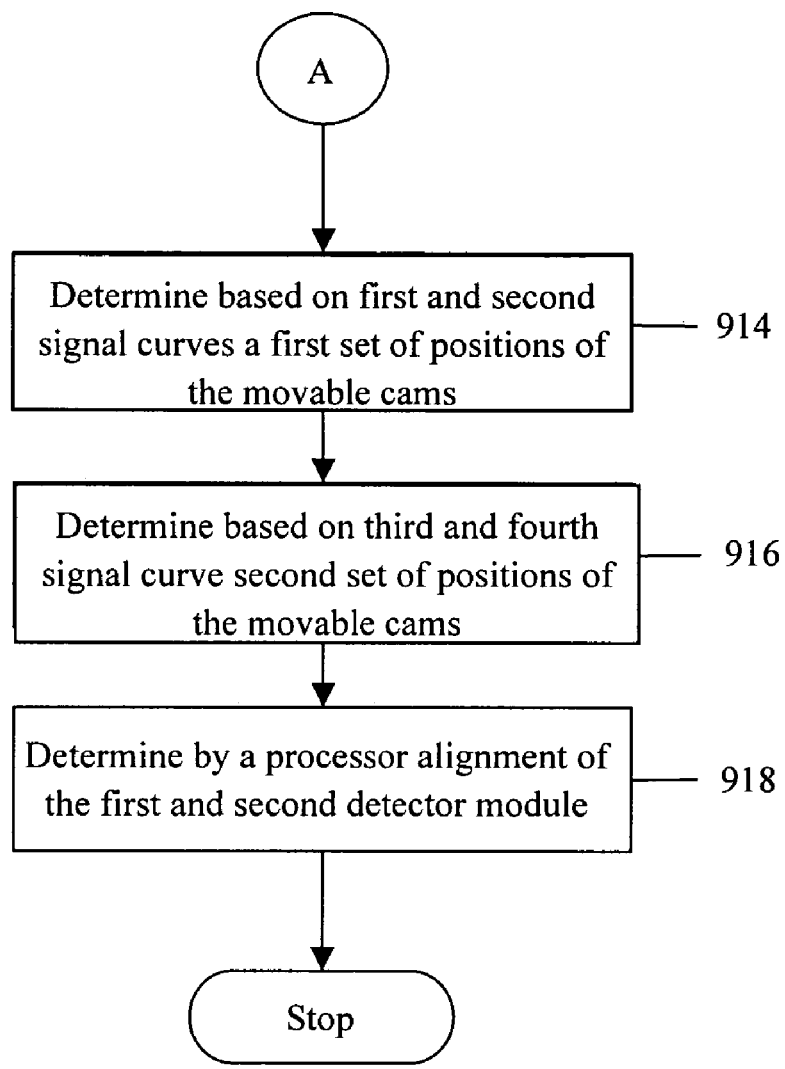
FIG. 10 is a continuation of the flowchart of FIG. 9.

FIG. 9 and FIG. 10 illustrate a flowchart of a method for measuring the alignment of a detector, in accordance with yet another embodiment of the invention. At 902, collimator 108 having movable cams 110 and 112 is positioned over detector 104. Movable cams 110 and 112 are initially placed so that detector cells 206 are under the umbra. Collimator 108 also collimates the x-rays to generate collimated x-ray beam 303. At 904, movable cams 110 and 112 sweep the edges of collimated x-ray beam 303 over first detector cell 406, second detector cell 408, third detector cell 410, and fourth detector cell 412. At 906, first detector cell 406 generates a first signal curve. The first signal curve contains values of signals generated by first detector cell 406 as an edge of collimated x-ray beam 303 is swept by movable cam 110 over first detector cell 406. At 908, second detector cell 408 generates a second signal curve. The second signal curve contains values of signals generated by second detector cell 408 as an edge of collimated x-ray beam 303 is swept by movable cam 112 over second detector cell 408. At 910, third detector cell 410 generates a third signal curve. The third signal curve contains values of signals generated by third detector cell 410 as an edge of collimated x-ray beam 303 is swept by movable cam 110 over third detector cell 410. At 912, fourth detector cell 412 generates a fourth signal curve. The fourth signal curve contains values of signals generated by fourth detector cell 412 as an edge of collimated x-ray beam 303 is swept by movable cam 112 over fourth detector cell 412. At 914, processor 106 determines a first set of positions of movable cams 110 and 112 at which the first and second signal curves measure same pre-specified signal intensity. In an embodiment of the invention, the first set of positions of movable cams 110 and 112 include a position x1 of movable cam 110 and a position x2 of movable cam 112 with respect to centerline 306. At 916, processor 106 determines a second set of positions of movable cams 110 and 112 at which the third and fourth signal curves measure the same pre-specified signal intensity. In an embodiment of the invention, the second set of positions of movable cams 110 and 112 include a position x3 of movable cam 110 and a position x4 of movable cam 112 with respect to centerline 306. Both x3 and x4 are positive values as measured from centerline 306 of collimated x-ray beam 303. In an alternative embodiment, the position x3 of movable cam 110 is determined when cam 110 sweeps a detector cell of second detector module 404 that is oppositely located on the other side of center-line 413 from fourth detector cell 412 but not at the same distance from center-line 413 as that of fourth detector cell 412. In another alternative embodiment, the position x4 of movable cam 112 is determined when cam 112 sweeps a detector cell of second detector module 404 that is oppositely located on the other side of center-line 413 from third detector cell 410 but not at the same distance from center-line 413 as that of third detector cell 410.

At 918, processor 106 determines whether first detector module 402 and second detector module 404 are aligned with each other based on the first and second set of positions. Processor 106 calculates a difference represented by an equation (2)

$$\{(x1-x2)/2-(x3-x4)/2\} \qquad (2)$$

Processor calculates the difference represented by equation (2) to determine whether the detector modules 402 and 404 are aligned with respect to each other. If the difference represented by equation (2) is zero, processor 106 determines that the detector modules 402 and 404 are aligned with respect to each other. If the difference represented by equation (2) is not zero, processor 106 determines that the detector modules 402 and 404 are not aligned with respect to each other. It is noted that 902 and 904 are performed by the motors under control of processor 106. It is also noted that 914, 916, and 918 are performed by processor 106. Finally, it is noted that equation (2) is independent of the shape of the collimated radiation beam 303 and, indeed, the profile of the collimated radiation beam 303 is continually changing as the collimator cams 110 and 112 are swept across the detector 104.

The value of equation (2) is independent of the shape of collimated x-ray beam 303. For example, the value of equation (2) does not need to be recalculated when the shape of collimated x-ray beam 303 changes from encompassing 6 rows of detector cells of first detector module 402 to 2 rows of detector module 402. As another example, the value of equation (2) stays the same before and after changing the shape of collimated x-ray beam from encompassing 4 rows of detector cells of second detector module 404 to 6 rows of detector module 404. Shape of collimated x-ray beam 303 is not a factor in determining the value of equation (2).

Various embodiments of the invention provide a method for measuring an alignment of a detector. The method measures the alignment of a plurality of detector modules of the detector at a module-to-module level.

Various embodiments of the invention provide a method for measuring an alignment of a detector. The method directly provides a measure of alignment of a plurality of detector modules, of the detector, in units of distance. Further, the measure of alignment is in the order of microns.

Although the various embodiments are described with respect to medical imaging, it should be understood that the various embodiments described herein are not limited to medical applications, but may be utilized in non-medical applications.

As used herein, an element or step recited in the singular and preceded with the word "a" or "an" should be understood as not excluding plural elements or steps, unless such exclusion is explicitly recited. Furthermore, references to "an" or "one" "embodiment" of the present invention are not intended to be interpreted as excluding the existence of additional embodiments that also incorporate the recited features.

The various embodiments of the methods for measuring an alignment of a detector and components thereof may be implemented as part of a computer system. The computer system may include a computer, an input device, a display unit and an interface, for example, for accessing the Internet.

As used herein, the term "computer" may include any processor-based or microprocessor-based system including systems using microcontrollers, reduced instruction set circuits (RISC), application specific integrated circuits (ASICs), logic circuits, and any other circuit or processor capable of executing the functions described herein. The above examples are exemplary only, and are thus not intended to limit in any way the definition and/or meaning of the term "computer".

The computer system executes a set of instructions that are stored in one or more storage elements, in order to process input data. The storage elements may also hold data or other information as desired or needed. The storage element may be in the form of an information source or a physical memory element within the processing machine.

The set of instructions may include various commands that instruct the processing machine to perform specific operations such as the processes of the various embodiments of the invention. The set of instructions may be in the form of a software program. The software may be in various forms such as system software or application software. Further, the software may be in the form of a collection of separate programs, a program module within a larger program or a portion of a program module. The software also may include modular programming in the form of object-oriented programming. The processing of input data by the processing machine may be in response to user commands, or in response to results of previous processing, or in response to a request made by another processing machine.

While the invention has been described in terms of various specific embodiments, those skilled in the art will recognize that the invention can be practiced with modification within the spirit and scope of the claims.

What is claimed is:

1. A method for measuring an alignment of a detector, said method comprising:
   positioning a collimator having movable cams and collimating a radiation beam;
   sweeping edges of the collimated radiation beam across the first cell and the second cell of the detector by successively moving the cams in a plurality of discrete positions;
   generating, by the first cell, a first signal curve as the collimated radiation beam is swept across the first cell;
   generating, by the second cell, a second signal curve as the collimated radiation beam is swept across the second cell;
   determining, based on the first and second signal curves, positions of the cams at which the first and second signal curves measure the same signal intensity; and
   determining, by a processor, the alignment of the detector with respect to the collimated radiation beam, said determining the alignment is based on a plurality of signals from the first cell of the detector and the second cell of the detector, and said determining the alignment is independent of a shape of the collimated radiation beam.

2. A method in accordance with claim 1 further comprising determining, by the processor, whether a plurality of columns of the detector are aligned with the collimated radiation beam.

3. A method in accordance with claim 1 fturther comprising determining, by the processor, whether a plurality of columns of the detector are aligned with each other.

4. A method in accordance with claim 1 further comprising determining, by the processor, whether a plurality of detector modules of the detector are aligned with each other, and each detector module includes a subset of a plurality of columns.

5. A method in accordance with claim 1 wherein said determining the alignment of the detector comprises determining the alignment from a difference between the positions of the cams.

6. A method in accordance with claim 1 wherein said determining the alignment of the detector comprises determining an average of the cam positions.

7. A method in accordance with claim 1 wherein said determining the alignment of the detector comprises determining $(x1-x2)/2$ from the positions of the cams, wherein x1 is a position of a first one of the cams that is on an opposite side of a centerline of the detector compared to a position x2 of a second one of the cams.

8. A method in accordance with claim 1 wherein sweeping edges of the collimated radiation beam across the first cell and the second cell of the detector comprises sweeping edges of the collimated radiation beam across the first cell and the second cell of a first detector module of the detector, and across a third cell and a fourth cell of a second detector module of the detector, wherein the third cell is at an oppositely located distance from a center-line of the second detector module as that of the fourth cell, said method further comprising:
   generating, by the third cell, a third signal curve as the collimated radiation beam is swept across the third cell;
   generating, by the fourth cell, a fourth signal curve as the collimated radiation beam is swept across the fourth cell;
   determining, based on the first and second signal curves, a first set of positions of the cams at which the first and second signal curves measure the same signal intensity;
   determining, based on the third and fourth signal curves, a second set of positions of the cams at which the third and fourth signal curves measure the same signal intensity; and
   determining, by the processor, whether the first and second detector modules are aligned with each other from the first and second sets of the positions of the cams.

9. A method in accordance with claim 8 wherein determining, by the processor, whether the first and second detector modules are aligned with each other from the first and second sets of the positions of the cams comprises determining whether a difference between an average of the first set of positions and an average of the second set of positions is zero.

10. A method in accordance with claim 1 wherein sweeping edges of the collimated radiation beam across the first cell and the second cell of the detector comprises sweeping edges of the collimated radiation beam across a first column of a first detector module of the detector and across a second column of a second detector module of the detector;
   wherein generating, by a first cell comprises generating, by a first set of cells of the first column of the detector, a first set of signal curves as the collimated radiation beam is swept across the first column;
   wherein generating, by a second cell comprises generating, by a second set of cells of the second column of the detector, a second set of signal curves as the collimated radiation beam is swept across the second column; and
   wherein determining, based on the first and second signal curves comprises determining, based on the first and second sets of signal curves, whether the detector modules are aligned with each other.

11. A system for measuring an alignment of a detector, said system comprising:
a collimator having one or more movable cams and configured to collimate a radiation beam, the cams configured to sweep edges of the collimated radiation beam across at least a first and a second cell of the detector by moving in a plurality of discrete steps, the first cell being configured to generate a first signal curve as the collimated radiation beam is swept across the first cell, the second cell being configured to generate a second signal curve as the collimated radiation beam is swept across the second cell; and
a processor configured to determine the alignment of the detector with respect to the collimated radiation beam based on a plurality of signals from a first cell of the detector and a second cell of the detector, wherein said processor is configured to determine the alignment independent of a shape of the collimated radiation beam, the processor being configured to determine, based on the first and second signal curves, positions of the cams at which the first and second signal curves measure the same signal intensity.

12. A system in accordance with claim 11 wherein said processor is further configured to determine whether a plurality of columns of the detector are aligned with the collimated radiation beam, the first cell is at an oppositely located distance from a center-line of the detector as that of the second cell from the center-line, and both the first and second cells are located along the same column of the detector.

13. A system in accordance with claim 11, wherein said processor is configured to determine whether a plurality of columns of the detector are aligned with each other.

14. A system in accordance with claim 11 wherein said processor is configured to determine whether a plurality of detector modules of the detector are aligned with each other, and each detector module includes a subset of a plurality of columns.

15. A system in accordance with claim 11 wherein said processor is configured to determine the alignment of the detector from a difference between the positions of the cams.

16. An x-ray imaging system comprising:
an x-ray source configured to generate an x-ray beam;
a detector comprising a plurality of modules and configured to detect the x-ray beam;
a collimator having movable cams and configured to collimate the x-ray beam, the cams configured to sweep edges of the collimated radiation beam across a first cell and a second cell of the detector by moving in a plurality of discrete steps, the first cell configured to generate a first signal curve as the collimated radiation beam is swept across the first cell, the second cell configured to a second signal curve as the collimated radiation beam is swept across the second cell; and
a processor configured to determine an alignment of the detector with respect to the collimated x-ray beam based on a plurality of signals from a first cell of the detector and a second cell of the detector, wherein said processor is configured to determine the alignment independent of a shape of the collimated radiation beam, the processor is further configured to determine, based on the first and second signal curves, positions of the cams at which the first and second signal curves measure the same signal intensity.

17. An x-ray imaging system in accordance with claim 16 wherein said processor is further configured to determine whether a plurality of columns of the detector are aligned with the collimated radiation beam, wherein the first cell is at an oppositely located distance from a center-line of the detector as that of the second cell from the center-line and both the first and second cells are located along the same column of the detector.

18. An x-ray imaging system in accordance with claim 16 wherein said processor is further configured to determine whether a plurality of columns of the detector are aligned with each other.

19. An x-ray imaging system in accordance with claim 16 wherein said processor is configured to determine whether a plurality of detector modules of the detector are aligned with each other, and each detector module includes a subset of a plurality of columns.

20. An x-ray imaging system in accordance with claim 16 wherein the processor is configured to determine the alignment of the detector by determining the alignment from a difference between the positions of the cams.

* * * * *